United States Patent [19]

Yuen

[11] Patent Number: 4,966,591
[45] Date of Patent: Oct. 30, 1990

[54] NEEDLE ASSEMBLY

[76] Inventor: Frank Yuen, 110-20 71st Ave., Forest Hills, N.Y. 11375

[21] Appl. No.: 260,197

[22] Filed: Oct. 20, 1988

[51] Int. Cl.$^5$ ............................................. A61M 5/32
[52] U.S. Cl. ................................... 604/192; 604/263; 206/365
[58] Field of Search ............... 604/192, 206, 263, 187, 604/198; 206/364, 365

[56] References Cited

U.S. PATENT DOCUMENTS

| | | | |
|---|---|---|---|
| 1,779,451 | 10/1930 | Sponsel | 604/197 |
| 3,884,230 | 5/1975 | Wulft | 604/198 |
| 4,664,259 | 5/1987 | Landis | 206/365 |
| 4,731,059 | 3/1988 | Wanderer et al. | 604/192 |
| 4,747,836 | 5/1988 | Luther | 604/198 |
| 4,820,277 | 4/1989 | Norelli | 604/192 |
| 4,850,977 | 7/1989 | Bayless | 604/198 |

FOREIGN PATENT DOCUMENTS 530857 1/1958 Italy .................... 604/192

*Primary Examiner*—C. Fred Rosenbaum
*Assistant Examiner*—Mark O. Polutta
*Attorney, Agent, or Firm*—Collard, Roe & Galgano

[57] ABSTRACT

A needle assembly for use in withdrawing bodily fluids has a body and a hollow needle extending through the body along a centrally located axis therethrough. The needle has a first end extending outwardly along the axis from a first side of the body and a second end extending from a second side of the body opposite the first side. The two cover elements are pivotally connected to the body for rotation toward and away each other in a plane containing the needle about two pivot points thereon. The cover elements have free ends extending outwardly from the body. Each cover element has a longitudinal extending interior cavity with an open side. This cavity extends beyond the tip of the first end of the needle so that when the two cover elements are rotated towards one another into a closed position, the needle is entirely surrounded by an enlarged cavity. When the needle is to be exposed, the cover elements are rotated away from one another into an open position exposing the tip of the needle. A latch element is provided to lock the cover elements in the closed position to prevent the accidental movement of the cover assemblies to the open position.

4 Claims, 1 Drawing Sheet

NEEDLE ASSEMBLY

BACKGROUND OF THE INVENTION

1. Field of the Invention

The invention relates to a needle assembly for use in drawing bodily fluids, such as blood. More particularly the needle assembly is designed so that the free ends of the needle are covered before use and may be covered after use in a manner which greatly reduces the risk of accidental puncture wounds.

2. Description of the Prior Art

Needle assemblies for drawing bodily fluids, in particular blood, are well known in the art. In general, these assemblies include a needle having a first end for puncturing the vein of a patient, and a second end for insertion into a evacuated, sealed empty container for receiving the patients blood. After a blood sample has been taken, the needle assembly is removed from the container now containing the blood and discarded.

As is well known, the epidemic of the Acquired Immuno Deficiency Syndrome (AIDS) has lead to concern that medical workers will be accidentally pricked by the needles after use. Accidents of this type are one documented means of becoming infected with AIDS. Therefore it has been considered of great importance in the art to avoid accidents, where doctors, nurses or other persons suffer puncture wounds from the use of needle assemblies. Presently, the safe disposal of used needle assemblies is considered a serious problem in the art. A recent article in the *New England Journal of Medicine* entitled "Rates of Needle-Stick Injury Caused by Various Devices in a University Hospital", published Aug. 4, 1988, highlights the fact that of the 326 injuries studied, 35 percent were caused by disposable syringes and 26 percent were caused by intravenous tubing and needle assemblies. Devices that required disassembly had rates of injuries of over 5 times the rate for disposable syringes In addition, one-third of the injuries were related to recapping. The article concluded that "Devices should be designed so that the workers hands remain behind the needle as it is covered, the needle should be covered before disassembly of the device and the needle should remain covered after disposal." Although this article documented the risk of needle-stick injuries, it did not propose any specific needle assembly designs for reducing such risk.

In order to prevent the occurrence of puncture wounds, where needle-stick injuries were accidentally self-inflicted by doctors or nurses, there has been some effort to provide simple methods for immediately covering the needle after use. U.S. Pat. No. 4,702,738 addresses this problem by disclosing a disposable hypodermic syringe with a retractable lockable sheath. Other patents, such as 4,356,822 also disclose a syringe assembly having a sheath that can be extended to cover the needle but which cannot be locked in the extended position. In addition, U.S. Pat. Nos. 4,237,882, 4,416,663, 4,573,972, 4,731,059, 4,139,009 and 3,967,621 also disclose syringe assemblies with various means for protecting the needle either before or after use. In addition, copending Application Serial No. 232,014 filed and owned by the inventor of the present invention also teaches a sheath assembly for protecting the exposed hypodermic needle.

SUMMARY OF THE INVENTION

It is an object of the present invention to provide a needle assembly wherein the needle is protected before and after use to prevent needle prick accidents involving the used needle.

It is another object of the invention to provide a disposable needle assembly wherein the needle is protected before use by a pivotal cover which can be pivoted to an open position to expose the needle for use and which can then be pivoted from a position behind the needle tip into a closed position after use.

It is a further object of the present invention to provide a needle assembly which is simple in design, economical to manufacture and which can be used in accordance with standard accepted medical procedures.

Accordingly, these and related objects are achieved by a needle assembly of the type which is intended to draw bodily fluids, especially blood, from a patient and then be discarded after a single use. The needle assembly includes a body having a hollow needle extending therethrough along an axis centrally located within the body. The needle has a first end extending outwardly along the axis from a first side of the body and a second end extending along the axis from a second opposite side of the body. At least one cover element is pivotally connected to the body for rotation from a closed to an open position about a pivot point thereon in a plane containing the centrally located axis. The cover element has a free end extending outwardly from the body beyond a tip portion of the needle located at the free end of the first end thereof. The cover element has an interior cavity therein with an open side facing inwardly. The cavity is capable of receiving the needle and covering the tip thereof when the cover element is in a closed position.

The needle assembly preferably uses two cover elements both pivotally attached to the body and rotatable towards one another into a closed position. These cover elements also include a cavity with an open side. Thus, when the cover elements are closed, they contact one another to form an enlarged cavity surrounding the first end of the needle. The two cover elements can be pivoted away from one another into an open position exposing the tip of the needle. A deflectable arm and latch are utilized to lock the two cover elements in the closed position after use.

The needle normally has a second end extending outwardly from a second side of the body along the same axis but in a direction opposite to the first end thereof. In use, this needle is designed to puncture an evacuated container and transmits the body fluids thereto after the first end of the needle is inserted into a patient's vein. It is contemplated that two additional cover elements be provided on the second side of the body. These two additional cover elements are pivotally connected to the body for rotation toward and away from each other in the same plane as the first two cover elements about an additional pair of pivot points thereon. Thus, both the first and second end of the needle may be selectively covered or exposed as desired.

The two cover elements on either the first or second side of the body also include a deflectable arm located on one of the cover elements. The deflectable arm has a hook element on a free end thereof for engaging a latch element on the second cover element when the cover elements are in a closed position. The hook element on the end of the arm being deflectable out of engagement with the latch element on the second cover to permit the cover elements to move away from one another to the open position.

These and other objects and advantages of the present invention will become apparent from the following description of the accompanying drawing which discloses one embodiment of the present invention. It is to be understood that the drawing is to be used for purposes of illustration only, and not as a definition of the invention.

BRIEF DESCRIPTION OF THE DRAWING

In the drawing, wherein similar reference characters denote similar elements throughout the several views:

FIG. 1 is a isometric view of the needle assembly of the present invention with the cover elements thereof in a closed position;

FIG. 2 is a plan view of the needle assembly of the present invention with the cover elements thereof in an open position;

DESCRIPTION OF THE PREFERRED EMBODIMENT

Figure 3:
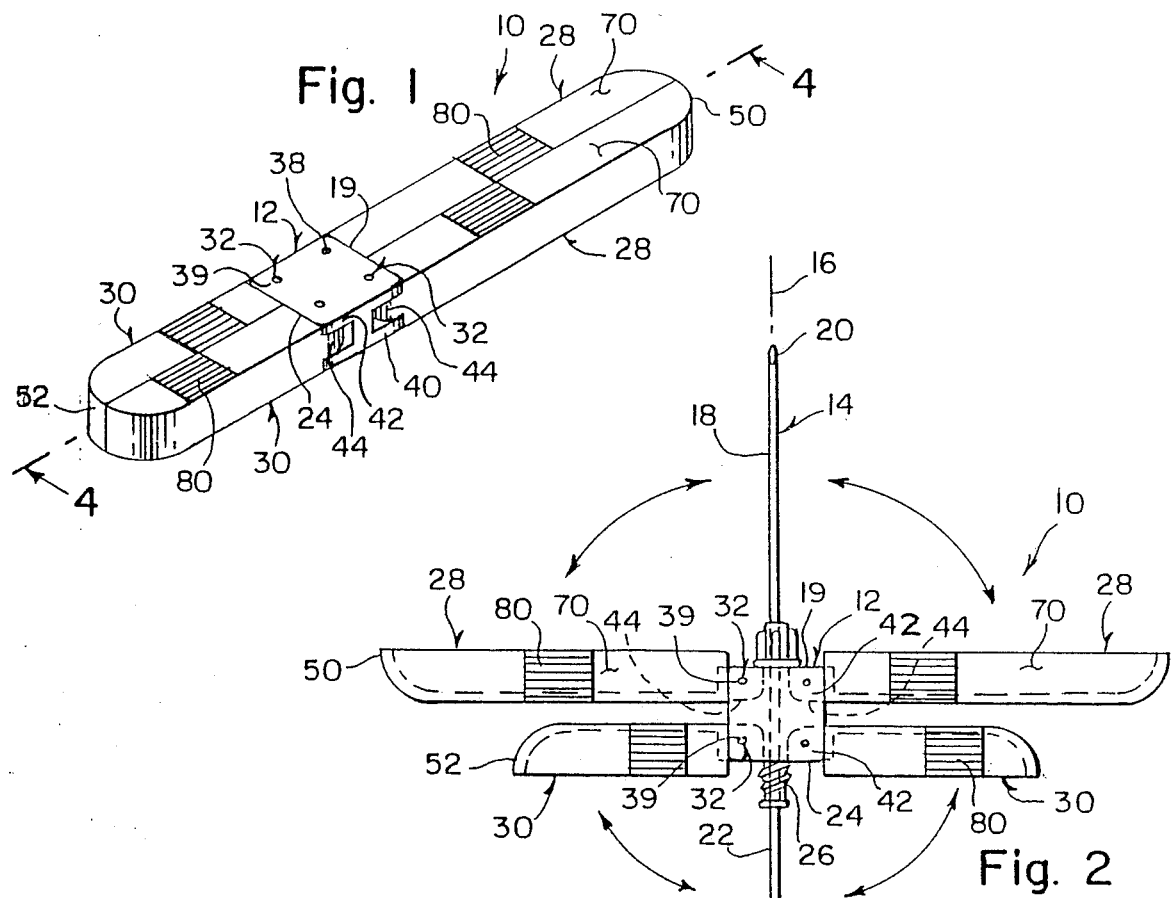
FIG. 3 is an enlarged isometric view of the end portion of the cover elements of the present invention including a locking system for holding the cover elements in a closed position.

Referring to FIGS. 1 through 4, there is shown a needle assembly of the present invention, generally denoted as 10, which includes a body 12 through which a hollow needle 14 passes along an axis 16. Needle 14 has a first end 18, with a tip 20, extending from a first side 19 of body 12. Tip 20 of needle 14 is adapted to be inserted inside a patient's body, such as into a vein, in order to draw blood. Needle 14 has a second end 22 extending from a second side 24 of body 12 which is opposite first side 19.

It has been standard practice to utilize a threaded portion 26 adapted to be screwed into an evacuated container (not shown) such that second end 22 of needle 14 pierces an elastomeric diaphragm sealing the container. Normally needle 14 is made of a single hollow tube which extends through body 12 along axis 16.

Prior to use first end 18 and second end 22 of needle 14 are enclosed by at least one, and preferably two cover elements 28 and two cover elements 30 respectively Each pair of cover elements 28, 30 are pivotally connected to body 12 by pivot pins 32. The ends 36 and 38 of pivot pins 32 are captured within holes 39 of leg portions 40 and 42 of body 12 respectively. Pivot pins 32 are designed so that they cannot become disengaged from leg portions 40, 42. This can be accomplished by making the diameter of pivot pin 32, extending between legs 40 and 42, wider than the diameter of holes 39 in legs 40, 42. However, it is equally advantageous for ends 36 and 38 of pivot pin 32 to be deformed, after installation in holes 39, such that a cap portion is formed in engagement with the outer surfaces of legs 40 and 42. In either case the pivot pins are retained within body 12. Cover elements 28, 30 include an extension 44 fixedly attached thereto. Extension 44 includes a hole 46 which receives the pivot pin 32 and is thereby rotatably captured between legs 40, 42 of body 12 by pins 32. It can be seen that after cover elements 28, 30 are assembled the two cover elements 28 and the two cover elements 30 may be rotated towards or away from one another about pivot pins 32.

Figure 4:
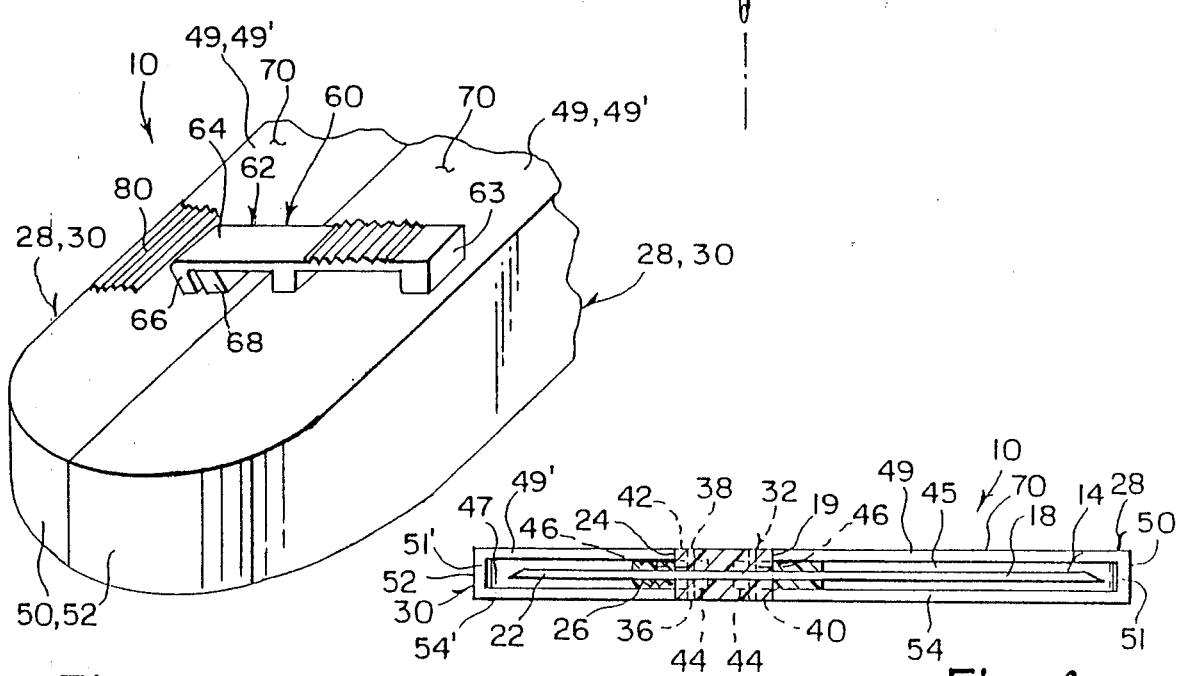
FIG. 4 is a cross-sectional view of the needle assembly shown in FIG. 1 along line 4—4.

Referring to FIG. 4 there is shown the interior of cover elements 28 and 30. The interior of cover elements 28 is essentially the same as element 30, except that normally cover elements 28 are longer than cover element 30 since the first end 18 of needle 14 is longer than second end 22. Cover elements 28 and 30 each have an interior cavity 45 and 47, spaced inwardly of free ends 50, 52 respectively which cavity is surrounded on three sides by walls 49, 49', 51, 51' and 54, 54'. Cavities 45 and 47, defined by walls 49, 51 and 54 and 49', 51' and 54' respectively, have an inwardly facing open side such that when the two cover elements 28 are in a closed position the edges of corresponding walls 49, 51 and 54 thereon contact one another forming an enlarged cavity capable of surrounding first end 18 of needle 14. Likewise the two cover elements 30 may be rotated in the same plane so that when in a closed position the edges of walls 49', 51' and 54' contact one another forming an enlarged cavity capturing second end 22 of needle 14.

Since the closed free end 50 of the two cover elements 28 extends beyond the tip 20 of needle 14 when covers 28 are in a closed position first end 18 is totally surrounded by cavity 45 and the tip 20 is enclosed. Legs 40, 42 are spaced a predetermined distance apart based on the thickness of extension 44 and define an opening with a depth sufficient to allow extension 44 to rotate therebetween. Preferably the two cover elements 28 may be rotated away from one another to an open position a distance that is sufficient to allow the edges of walls 49, 51 and 54 to form an angle of 90 degrees with respect to axis 16. Likewise the two cover elements 30 may be rotated such that the edge surface of walls 49', 51' and 54' also forms an angle of 90 degrees with respect to axis 16.

Referring to FIG. 3, there is shown a latch assembly of the present invention capable of maintaining cover elements 28 or cover elements 30 in a closed position. The latch assembly, generally denoted as 60, includes a deflectable arm 62 having an end 63 which is fixedly coupled to a first of the cover elements 28, 30 and has a movable free end 64 extending across the edge of walls 49 or 49' and terminating in a hook portion 66. A latch element 68 is fixedly attached to the other cover element of cover elements 28, 30. Hook portion 66 and latch element 68 are preferably inclined away from the edge of walls 49, 49'. Thus, when the two cover elements 28, 30 are in the closed position, hook element 66 rides up over latch element 68 causing the upward deflection of free end 64 of arm 62. Then, because of the resiliency of arm 62, hook 66 springs downwardly thereby capturing element 68 and preventing the movement of the two cover elements 28, and the two cover elements 30 away from one another to the open position. Of course, should such movement be desired, hook 66 may be lifted out of engagement with latch 68 so that the cover elements may be moved away from one another.

To use the needle assembly of the present invention one would move the two cover elements 30 away from one another to the open position as shown in FIG. 2. Then needle 22 would be inserted into an evacuated fluid container in the well known manner. The user would then move the two cover elements 28 into the open position thereby exposing first end 18 of needle 14 which can then be used to draw blood from a patient. It should be noted that one advantageous feature of the present invention is that tip 20 is beveled, which bevel has its face aligned with the plane of rotation of cover elements 28 such that the bevel faces the same direction as the surface 70 of cover elements 28. This allows the user to determine the orientation of the face of the bevel on the needle tip even after the same has been inserted into the patient.

After removal of the blood or other bodily fluid from the patient first end 18 is withdrawn from the patient and the two cover elements 28 are rotated into the closed position thereby completely surrounding first end 18. Latch assembly 60 assures that the two cover elements 28 stay in the closed position. The user then removes the second end 22 of needle 14 from the container and moves the two cover elements 30 to their closed position. Normally elements 30 include a similar latch assembly 60 in order to maintain the two cover elements in the closed position. At this point the needle no longer has any use and may be discarded without any fear of accidental puncture wounds being inflicted on individuals who may inadvertently come in contact with the needle assembly.

As can be seen in FIGS. 1-3 cover elements 28 and 30 may include finger gripping portions 80 which facilitate the opening and closing of the cover elements. While elements 80 are shown as ridges molded into the surfaces of cover elements 28, 30, which are normally made of molded plastic, the actual contour of elements 28, 30 may be curved in order to facilitate pulling the elements from the closed to the open position or vice versa.

While the use of two individual cover elements 28 or 30 are illustrated to cover each end of needle 14, it can be seen that one cover element 28 or 30 could be utilized if the cavity thereof and the pivot point on body 12 is located such that the single cover element may be pivoted to a closed position completely surrounding either first end 18 or second end 22 of needle 14.

While one embodiment and example of the present invention has been illustrated and described, it is obvious that many changes and modifications may be made thereunto without departing from the spirit and scope of the invention.

What is claimed is:

1. A needle assembly for withdrawing body fluids, comprising:
   a body having a first side and a second opposite side and a first end and a second opposite end, and a centrally-disposed aperture extending through said body generally normally with respect to said first and second ends to define a longitudinally-extending central axis, said first side being generally parallel to said second side of said body; a vertical member connecting said first side to said second side in a spaced apart manner, such that the cross-section of said body along said central axis is I-shaped;
   a hollow needle extending through said body aperture and having a first needle end portion with a tip extending outwardly along said central body axis from said first end of said body, and a second needle end portion with a tip extending outwardly along said central body axis from said second end of said body, said needle tips each having a beveled face oriented to face one of said sides of said body;
   a first pair of cover elements, each of which has a longitudinally-extending interior channel, and each of which cover elements has an extension means for pivotally coupling said cover elements to said body and said extension means disposed adjacent said first end thereof by being positioned and held within the I-shaped cross-section defined by the space between the first side of said body, the connecting vertical member, and the second side of said body;
   and a second pair of cover elements, each of which has a longitudinally extending interior channel, and each of which cover elements has an extension means for pivotally coupling said cover elements to said body and said extension means disposed adjacent said second end thereof by being positioned and held within the I-shaped cross-section defined by the space between the first side of said body, the connecting vertical member, and the second side of said body;
   said pairs of cover elements being pivotable between an open position, in which said cover elements of each pair extend wing like in opposition directions generally normally to said central axis, and a closed position in which said cover elements of each pair abut one another with their respective channels cooperating to enclose the respective needle end portion therebetween, whereby when said cover elements are disposed in said wing like open position, they are in tandem back to back relationship and allow the user to determine the orientation of the beveled face of the needle; and
   means for locking said first and second pairs of said cover elements in said closed position.

2. The needle assembly as set forth in claim 1, further comprising pins for pivotally holding said extension means positioned within said I-shaped cross-section.

3. The needle assembly as set forth in claim 1, wherein said means for locking said first and second pairs of said cover elements in said closed position includes a movable arm fixedly coupled to a first cover element and having a hook element on a free end thereof engaging a latch element on a second cover element when the two cover elements are in a closed position, said hook element of said arm being movable out of engagement with said latch element of said second cover element to permit said two cover elements to move away from one another.

4. The needle assembly as set forth in claim 1, wherein said means for locking said two cover elements in said closed position includes a movable arm fixedly coupled to a first cover element and having a hook element on a free end thereof engaging a latch element on a second cover element when the two cover elements are in a closed position, said hook element of said arm being movable out of engagement with said latch element of said second cover element to permit said two cover elements to move away from one another.

* * * * *